US00PP10846P

United States Patent [19]

Cully

[11] Patent Number: Plant 10,846

[45] Date of Patent: Mar. 30, 1999

[54] LACEBARK ELM TREE NAMED 'ZETTLER'

[76] Inventor: Earl Cully, R.R. #5, Box 84A, 846 Hoagland Rd., Jacksonville, Ill. 62650

[21] Appl. No.: 862,720

[22] Filed: May 23, 1997

[51] Int. Cl.[6] ..... A01N 5/00

[52] U.S. Cl. ..... Plt./221

[58] Field of Search ..... Plt./53.3

[56] References Cited

U.S. PATENT DOCUMENTS

P.P. 5,554 9/1985 King ..... Plt./53.3
P.P. 6,983 8/1989 Karnosky ..... Plt./53.3
P.P. 7,240 6/1990 Rey ..... Plt./53.3
P.P. 7,551 6/1991 Glenn ..... Plt./53.3
P.P. 7,552 6/1991 Glenn et al. ..... Plt./53.3

*Primary Examiner*—Douglas W. Robinson
*Assistant Examiner*—Kent L. Bell

[57] ABSTRACT

A new and distinct lacebark elm named 'Zettler', characterized by its upright, medium oval growth habit, its beautiful exfoliating bark color and texture, its extreme winter hardiness, and its ability to withstand wind and ice, without breakage.

5 Drawing Sheets

The present invention comprises a new and distinct cultivar of lacebark elm tree, botanically known as *Ulmus parvifolia* and referred to by the cultivar name 'Zettler'.

The initially discovered tree is growing in a cultivated area on the home grounds of inventor Earl Cully, R.R. 5, Box 84A, 846 Hoagland Road, eight miles southeast of Jacksonville, Il, in Morgan County, in Township 14, Range 10.

The new cultivar 'Zettler' is the result of seedling selections made in 1975, when the inventor selected approximately 100 superior seedlings out of a population of 20,000 one-year-old *Ulmus parvifolia.* Of these 100selected seedlings, ALL BUT ONE were eventually eliminated because of winter damage, complete winter kill, canker disease or poor habit of growth. This one individual tree, now named 'Zettler', developed an upright habit of growth, grew with great vigor, was extremely winter hardy, and developed a beautiful bark color and texture (FIG. 1).

The new cultivar has proven to be highly resistant to canker disease and Dutch Elm disease. It has never been bothered by the Elm Leaf Beetle. Its high resistance to canker disease is probably due to its ability to harden early in the fall; as a result, the new cultivar does not suffer bark and cambium damage when the first blast of cold hits in late November or early December. (Cambium damage from low winter temperatures creates wounds where canker fungi spores can enter the tree.)

The 'Zettler' Lacebark Elm is very adaptable to a variety of soil types. It will tolerate extreme heat and drought without showing stress and will retain a full canopy of beautiful foliage during this stressful period.

The medium oval growth habit of the 'Zettler' cultivar lends itself well for planting on city streets, on home lawns, in parks, or in any confined area where other trees would soon become overgrown.

The following characteristics in combination distinguish the new tree named 'Zettler' from other trees of the species, including the patented cultivars 'Elmer I' (U.S. Plant Pat. No. 7, 551), 'Emer II' (U.S. Plant Pat. No. 7,552), 'King's Choice' (U.S. Plant Pat. No. 5,554), 'Golden Rey' (U.S. Plant Pat. No. 7,240), and 'ARoss/Central Park' (U.S. Plant Pat. No. 6,983).

1. Compared to the species and the above-mentioned patented cultivars, the 'Zettler' elm is far more winter hardy, withstanding temperatures of −28°F. to −30°F. without damage. During October 1991, temperatures were warm for the entire month, but on October 31, dropped into the teens. On November 3, a record low was recorded of −1° F. Many tree species were badly damaged from this arctic blast of air. Although some species, such as green ash *Fraxinus pennsylvanica,* were killed to the ground, the cultivar 'Zettler' suffered only slight damage and recovered rapidly the following spring. Based on its withstanding this early blast of arctic air, and other winter low temperatures of −28° F. to −30° F. during the past twenty-one years, the new cultivar named 'Zettler' would be reliably hardy in the lower one-half of Zone 5A and all of Zone 5B (USDA Plant Hardiness Zone Map).

2. The new cultivar is a vigorous grower. The inventor has observed 3' to 4' of new growth on young asexually propagated trees in one growing season. Growth habit is upright, medium oval in form, and at twenty-one years of age is 42' in height with a limb spread of 23' (FIG. 1 and FIG. 5). This medium oval growth habit is distinctly different from the above-mentioned patented cultivars.

3. The tree is highly resistant to wind and ice. It has never had a limb break from wind or ice during the twenty-one years its has been under test.

4. The foliage of the 'Zettler' elm is a lustrous dark green on the upper surface of the leaf and a lighter green on the underside (FIG. 2).

5. Bark color and texture are outstanding. Exfoliation of the bark starts when the trunk reaches a diameter of 2½" to 3" (FIG. 3). The greenish-gray bark, as it exfoliates, exposes an inner bark in shades of silver and cinnamon (FIG. 4).

PROPAGATION

The new cultivar was first propagated by chip budding onto *Ulmus parvifolia* seedling root stock. This method of asexual propagation was not successful because of delayed incompatibility between scion and root stock. Later, the new tree was asexually reproduced in tissue culture at Microplant Nurseries in Gervais, Oreg.; Plants Unlimited, Afton, Va.; and now at Meadow Lake Nursery, McMinnville, Oreg. Softwood cuttings are also being taken from tissue cultured plants and these cuttings are rooting well. Asexual propagation by tissue culture of the new cultivar named 'Zettler' has proved to be very consistent and effective.

DETAILED BOTANICAL DESCRIPTION

In the following description, color references are made to The Royal Horticultural Society Colour Chart except where general terms of ordinary significance are used.

BRIEF DESCRIPTIONS OF THE DRAWINGS

The accompanying colored photographs illustrate the overall appearance and color of the new lacebark elm tree, showing the colors as true as it is reasonably possible to obtain in colored reproductions of this type. Actual bark, lenticel, and foliage colors may differ from bark, lenticel, and foliage colors in the photographs due to light reflectance.

The Plant

Figure 1:
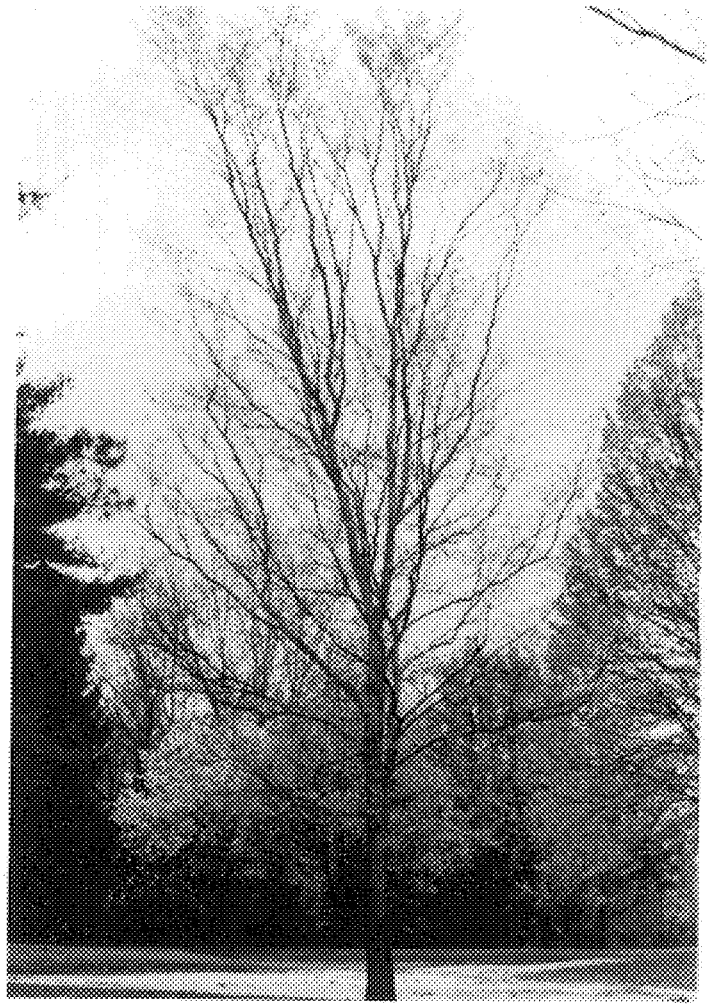
FIG. 1 depicts the initially discovered tree named 'Zettler'.
Figure 2:
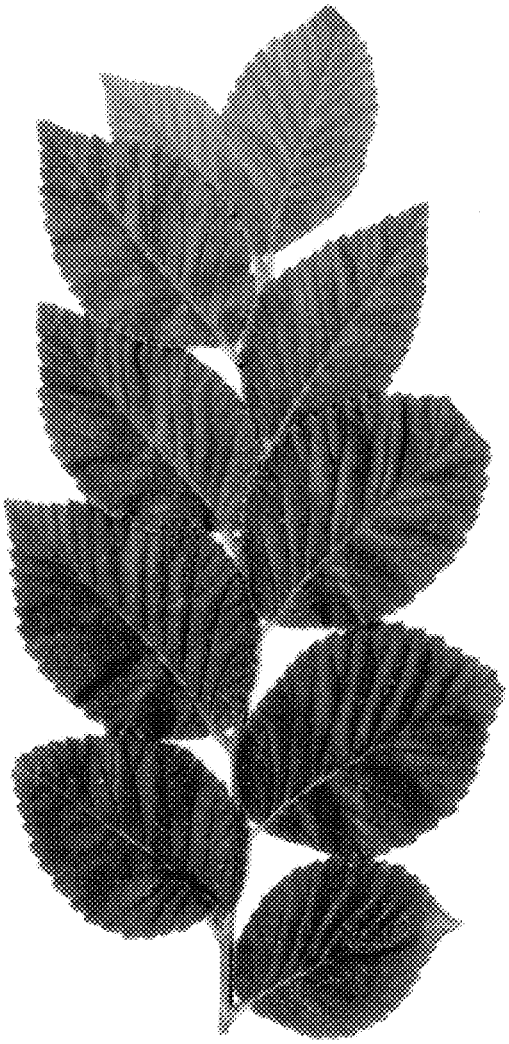
FIG. 2 depicts a close up view of the actual leaf size, color and arrangement on twigs.
Figure 3:
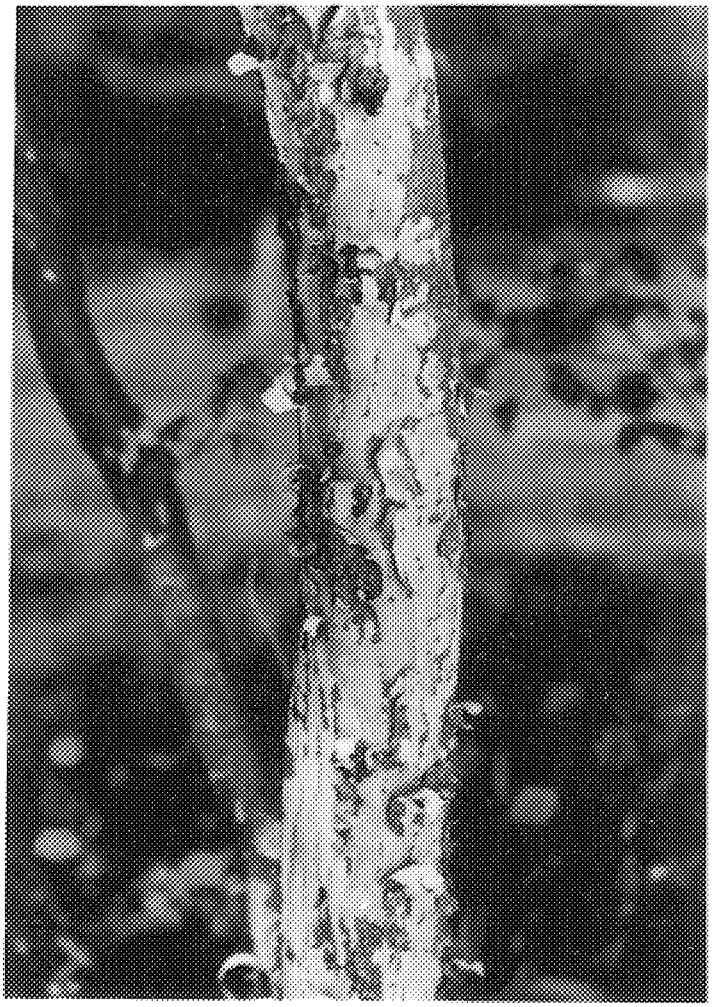
FIG. 3 depicts the bark texture and color and lenticels of 'Zettler' on a three-inch caliper asexually reproduced tree.
Figure 4:
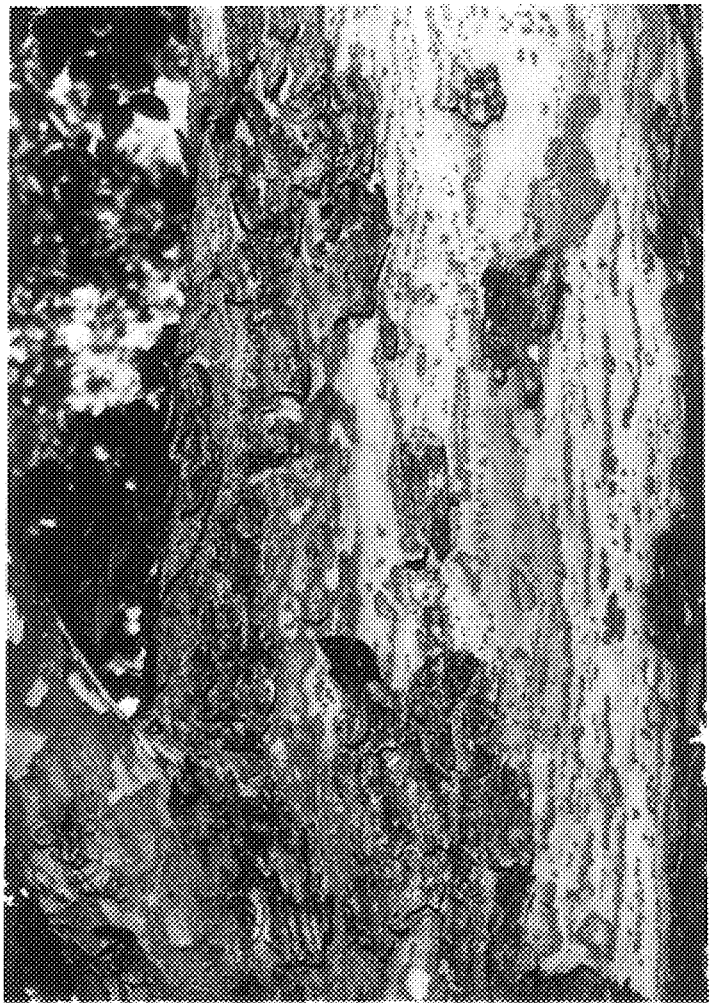
FIG. 4 depicts the bark texture and color and lenticels.
Figure 5:
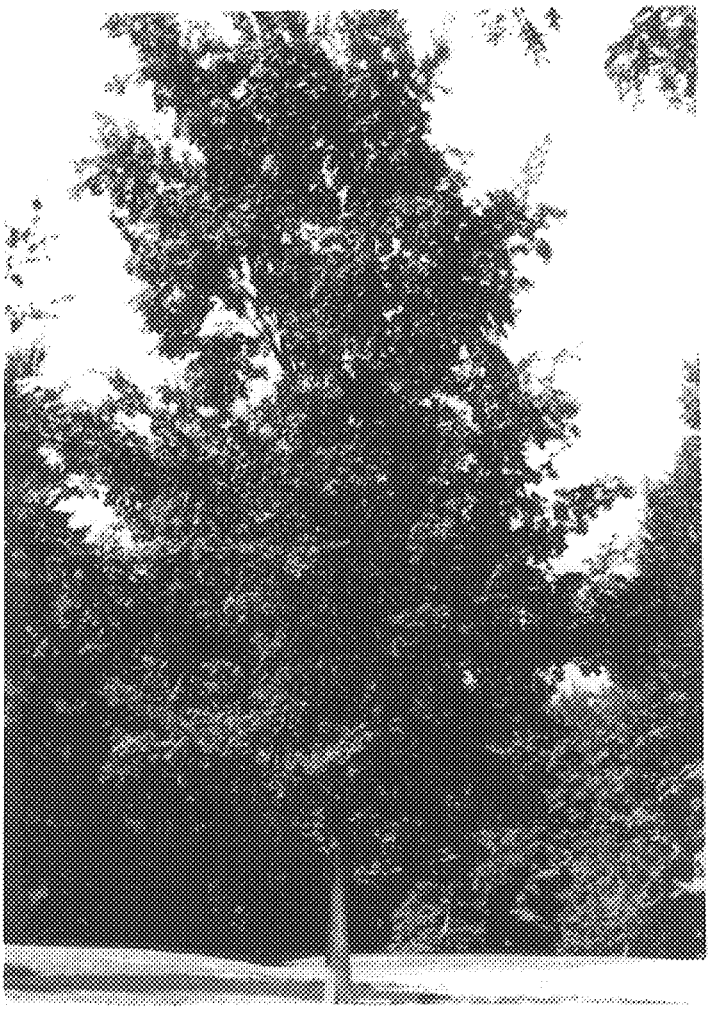
FIG. 5 depicts the initially discovered tree with new growth.

Form: Tree.
Shape: Decurrent, upright-oval.
Height: 12.8 m (42').
Trunk size: DBH (diameter at breast height) 25.1 cm (9.9")
Bark: Outer bark: Exfoliating, greenish-gray; fissures more or less vertically; thin; curves upward at edges, becoming shaggy; lenticels at fissures. Inner bark: mottled; colors vary from silver (156B) to cinnamon (166C/D, 168D); lenticels rust colored (171B), vertical, in single and double rows, contribute to cracking of outer bark.
Growth rate: Moderate (~61 cm {2'} per year)
Strength: Excellent! It has never had any limb breakage from wind or ice.
Branches:
*Angle of attachment.*—15–80°, average 48.35°; at 4.9 m (16') the trunk splits into two main branches with an approximate 20° angle. Branches arising from the two main branches tend to have narrow (20°–30°) crotches.
*Spacing.*—Regular.
*Color.*—Branch color changes with size Size: >10 cm (4"). Bark: Mottled; colors vary; predominant color is gray (156A). Lenticels: Orange (172A), begin to become vertical. Quantity: scattered, prominent. Size: <10 cm (4"). Bark: Silver (190A), smooth with vertical striations. Lenticels: Conspicuos, orange (171B) singular 3–7 mm, horizontal.
Leaves:
*Length.*—3.8–5.9 cm, average 5.2 cm.
*Width.*—2.2–3.4 cm, average 2.7 cm.
*Form.*—Elliptical to ovate or obovate, base unequally rounded, occasionally cordate; apex acute to acuminate.
*Margin.*—Simply or nearly simply serrate.
*Texture.*—Leathery; glossy; glabrous above, pubescent beneath while young.
*Quantity.*—Abundant, imbricate on branch.
*Mature color.*—Upper side: lustrous dark green (137A). Lower side: lighter green(137B).
*Immature color.*—Upper side: 143B/144A/144B/145A. Lower side: Close to but lighter than the upper side.
*Fall color.*—Upper/Lower sides: Various shades of yellow, purple, pink, and red. Fall colors do not occur every season.
*Petioles.*—Length 3–4 mm, average 3.69 mm.
*Ribs and veins.*—10–14 pairs.
*Thorns.*—None.
*Spines.*—None.
*Prickles.*—None.
Buds: (Vegetative) small (2–3 cm), conical, reddish-brown, slightly pubescent.
Flowers: Typical of the species.
Fruit: Samara; ripen in fall, abscise in October; typical of the species in size and color.

It is claimed:

1. A new and distinct lacebark elm tree named 'Zettler' as illustrated and described.

* * * * *